United States Patent
Chordia et al.

(10) Patent No.: US 6,908,557 B2
(45) Date of Patent: Jun. 21, 2005

(54) COLLECTION SYSTEM FOR CHROMATOGRAPHIC SYSTEM

(75) Inventors: Lalit Chordia, Pittsburgh, PA (US); Harbaksh Sidhu, Cranberry Township, PA (US)

(73) Assignee: Thar Technologies, Inc., Pittsburgh, PA (US)

(*) Notice: Subject to any disclaimer, the term of this patent is extended or adjusted under 35 U.S.C. 154(b) by 78 days.

(21) Appl. No.: 10/602,941

(22) Filed: Jun. 24, 2003

(65) Prior Publication Data

US 2004/0262222 A1 Dec. 30, 2004

Related U.S. Application Data

(60) Provisional application No. 60/391,048, filed on Jun. 25, 2002.

(51) Int. Cl.[7] .............................................. B01D 15/08
(52) U.S. Cl. ...................... 210/659; 210/634; 210/656; 210/198.2
(58) Field of Search ................ 210/634, 635, 210/656, 659, 198.2; 422/70, 285; 436/161

(56) References Cited

U.S. PATENT DOCUMENTS

| | | | |
|---|---|---|---|
| 4,478,720 A | | 10/1984 | Perrut |
| 5,205,987 A | | 4/1993 | Ashraf-Khorassani |
| 5,241,998 A | * | 9/1993 | Ashraf-Khorassani ....... 141/67 |
| 5,458,783 A | * | 10/1995 | Levy et al. ................. 210/659 |
| 5,601,707 A | | 2/1997 | Clay et al. |
| 5,614,089 A | | 3/1997 | Allington et al. |
| 5,750,027 A | | 5/1998 | Allington et al. |
| 6,086,767 A | | 7/2000 | Walters et al. |
| 6,149,814 A | | 11/2000 | Allington et al. |
| 6,294,088 B1 | | 9/2001 | Allington et al. |
| 6,309,541 B1 | | 10/2001 | Maiefski et al. |
| 6,355,164 B1 | | 3/2002 | Wendell et al. |
| 6,413,428 B1 | | 7/2002 | Berger et al. |
| 6,427,526 B1 | | 8/2002 | Davison et al. |
| 6,508,938 B2 | | 1/2003 | Maiefski et al. |
| 2002/0070169 A1 | | 6/2002 | Berger et al. |
| 2002/0070170 A1 | | 6/2002 | Berger et al. |
| 2002/0139752 A1 | | 10/2002 | Berger et al. |
| 2002/0144949 A1 | | 10/2002 | Berger et al. |

FOREIGN PATENT DOCUMENTS

EP 117057 9/2002

* cited by examiner

Primary Examiner—Ernest G. Therkorn

(57) ABSTRACT

The present invention provides a method and device for collecting and concentrating a desired compound from a chromatographic column exit stream. The collection chamber can be heated or cooled and washed in a forward or backward direction for efficient removal.

31 Claims, 1 Drawing Sheet

COLLECTION SYSTEM FOR CHROMATOGRAPHIC SYSTEM

CROSS-REFERENCE TO RELATED APPLICATION

This application claims priority to U.S. Provisional patent application Ser. No. 60/391,048 filed Jun. 25, 2002, teachings of which are incorporated herein by reference.

BACKGROUND OF THE INVENTION

The use of supercritical fluids in industrial processes has been growing at an ever-quickening pace. Replacing traditional, often hazardous and flammable, organic solvents with supercritical fluids has been a prime area of research. Carbon dioxide is a popular choice due to the fact that it is nontoxic, nonflammable, and inexpensive. An attractive feature of a supercritical fluid is that its density can be varied simply by changing the pressure or temperature. Therefore, all density-dependent properties, such as dielectric constant and solubility parameter, can be manipulated in this manner. These key features of supercritical fluids make them ideal candidates for use in extraction and chromatography applications.

In the chemical and pharmaceutical industries, the demand for purified compounds is increasing steadily. It has become highly desirable to obtain components of the highest available purity in the largest quantities. In many instances, high performance liquid chromatography (HPLC) has been the analytical method of choice for these types of separations. HPLC can be analytical or preparative in nature, the component levels varying depending on the application. In the case of preparative HPLC, a collection means is also employed for the sample fractions. However, a drawback to the use of HPLC is the fact that in many instances long elution times, as well as large of amounts of solvents are required for the process.

Supercritical fluid chromatography (SFC) has been introduced in the past decade as an alternative to HPLC. The technique employs a supercritical fluid, typically carbon dioxide, as the mobile phase. In many instances, an organic solvent is also present as a modifier in order to adjust the polarity of the mobile phase. Because supercritical fluids are known for their high diffusivities, this results in enhanced speeds and resolving power when compared to HPLC. The difference can be as much as an order of magnitude in some applications. Additionally, SFC systems can reequilibrate faster than HPLC systems and therefore can be ready to process other samples in a shorter time frame. Many of the advantages of SFC over HPLC are applicable to both analytical and preparative methods. However, much like HPLC, SFC also needs a means to collect the sample fractions, preferably multiple fractions, in an efficient, cost-effective manner.

Collection means for SFC have been explored in past research. For example, U.S. Pat. No. 6,413,428 (Berger et al.) and EP 117057 (Berger et al.) disclose a sample collection process for preparative SFC using a collection chamber consisting of test tubes. The system is automated in an embodiment. Sample collection is also discussed in U.S. Pat. No. 5,601,707 (Clay et al.), U.S. Pat. No. 6,086,767 (Walters et al.), U.S. Pat. No. 6,309,541 (Maiefski et al.), and U.S. Pat. No. 5,614,089 (Allington et al). While there are several mechanisms for analyte collection in SFC, there still exists a need which can collect all fractions more efficiently and concentrate the samples for further analysis. Implementing such a method would make the overall process of SFC much more cost-effective.

U.S. Pat. No. 5,205,987 (Ashraf-Khorassani et al.) disclosed a collection mechanism for off-line supercritical fluid extraction in which the analyte is gathered in a collection trap after being extracted. The collection means contained beads to trap the analyte and carbon dioxide was used to cool the trap. The analyte was then desorbed from the trap using an appropriate solvent. A vial was placed downstream from the trap to collect the analyte dissolved in the desorbing solvent. However, this patent does not address the issue of concentrating the samples. The object of the present invention is to apply the engineering fundamentals of this patent to a collection system for chromatography in which the samples are also collected at a higher concentration.

SUMMARY OF THE INVENTION

The present invention provides a method and device for collecting a desired compound from a chromatographic column exit stream comprising directing the stream to a collection chamber, cooling the collection chamber to a sub-ambient condition, collecting the compound for a duration to concentrate in the collection chamber, heating the collection chamber, washing the collection chamber with a desired solvent, and collecting the washing. The washing can be accomplished in both forward and backward directions for efficient removal from the collection chamber. The stream is directed to more than one collection chamber depending on detection of the stream component and time. The chromatographic exit stream contains a compressed fluid. The chromatographic exit stream contains one or more solvents. The compressed fluid is selected from the group consisting of carbon dioxide, water, ammonia, nitrogen, nitrous oxide, methane, ethane, ethylene, propane, butane, n-pentane, benzene, methanol, ethanol, isopropanol, isobutanol, monofluoromethane, trifluoromethane, dimethyl sulfoxide, acetonitrile, hydrofluorocarbons, chlorotrifluoromethane, monofluoromethane, hexafluoroethane, 1,1-difluoroethylene, 1,2-difluoroethylene, toluene, pyridine, cyclohexane, m-cresol, decalin, cyclohexanol, O-xylene, tetralin, aniline, acetylene, chlorotrifluorosilane, xenon, sulfur hexafluoride, propane and combinations thereof. The compressed fluid is carbon dioxide. The cooling of the collection chamber is accomplished through one or more of the following techniques: thermoelectric cooling, liquid nitrogen cooling, peltier cooling, or other fluidic cooling. The cooling of the collection chamber is accomplished through the pressure reduction of the compressed fluid. The heating of the collection chamber is accomplished through electrical or fluidic heating. The cooling and heating are accomplished rapidly. The collection chamber contains absorbing material. The collection chamber contains adsorbing material. The material inside the collection chamber is in particulate form, a liquefied gas or frozen gas. The collection chamber contains a removable cartridge. The cartridge is packed with one or more materials. The particles contain active or passive surface area for efficient retention. The heating of the collection chamber facilitates the removal of the compound from the collection chamber. The temperature of the collection chamber is controlled. Temperature control is achieved through a combination of the heating and cooling means. The amount of washing solvent to be used is defined. The compressed fluid is at or near supercritical conditions. The washings are collected in vials for further processing. The activities of the invention are automated through the use of mechanical arrangements, electrical or pneumatic pulses, logic controllers, microprocessors, and software programs. The detection of the component is accomplished through the use of one or more of the detectors selected from the group consisting of Mass spectroscopy detector, UV/VIS detector, Evaporative Light Scattering Detector, Flame Ionization detector, Fourier Transform Infrared Spectroscopy Detector, Infrared Detector and combinations thereof. The collection chamber can be cleaned with a solvent and dried for subsequent use. The cleaning can be accomplished through forward or backward flowing of the solvent.

The present invention also provides for a device for collecting a desired compound from a chromatographic column exit stream comprising a valve for directing the stream to a collection chamber, coolers for cooling the collection chamber to sub-ambient conditions to retain the compound in the collection chamber, heaters for heating the collection chamber, a mechanism for washing the collection chamber with a desired solvent, and a mechanism for collecting the washing. The mechanism for washing is automated and coordinated with the directing valve, collection chamber and washing solvent pump. The washing solvent pump is capable of pumping more than one solvent drawn from different sources at a defined composition. The defined composition is accomplished through the use of a series of valves. The components and fluidic connections can withstand pressures up to 1000 bar and the fluidic connections are made of stainless steel or an alloy capable of withholding up to 1000 bar.

DETAILED DESCRIPTION OF THE INVENTION

Figure 1:
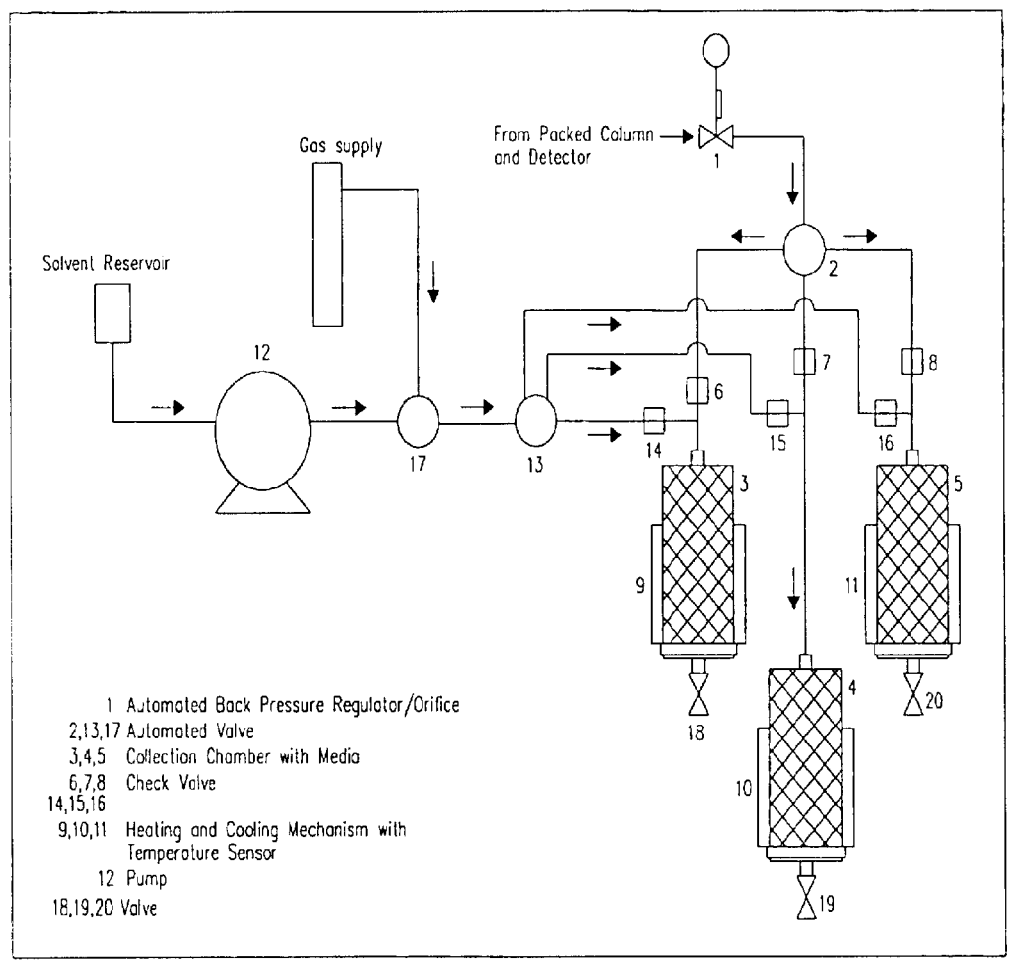
FIG. 1 is a schematic representation of one preferred embodiment of the invention that includes three collection chambers.

Definitions:

It is noted that as used in this disclosure and the appended claims the singular forms "a" "an" and "the" include plural reference unless the context clearly dictates otherwise. For example, a compound is intended to mean a single compound or a mixture of compounds, a solvent is intended to mean a single solvent or a mixture of solvents.

"At or near supercritical conditions" means being at a temperature between $0.2T_c$ and $5T_c$ and a pressure between $0.2P_c$ and $5P_c$.

"Collection chamber" means the place where a compound is collected.

"Sub-ambient" means below ambient temperature.

"Forward direction" means in the direction of the flow of the exit stream.

"Backward direction" means against the direction of the flow of the exit stream.

"Detection of the stream component" means detecting a chromatographic signal corresponding to a component and generating a signal for stream direction.

"Compressed fluid" means a fluid under pressure.

"Cartridge" means a modular enclosable device.

"Active surface area" means a chemically active surface.

"Passive surface area" means a chemically inactive surface.

"Electric cooling" means using electricity to cool an element.

"Peltier cooling" means application of a voltage to have a thermal effect.

"Fluidic cooling" means using a fluid to remove heat.

Description

The present invention describes a method and apparatus for the collection and recovery system for use with packed column chromatography applications including drug discovery or other high-throughput application. It is also applicable to analytical applications using a fluid that is near or above the critical point. The cryofocusing system is comprised of a mechanism for collection of an isolated, eluted compound or combination of compounds from a chromatographic column exit stream based on detector signal response and user's collection settings.

The desired compound or compounds eluted from a chromatographic column are detected using a detector and based on detector signal response, the flow stream is directed to one or more collection chambers using a switching valve. The detector signal response on elution of the compound or compounds is processed using a signal processor. The parameters of the signal processor for collection can be programmed by the user to collect one or more compounds in a collection chamber for concentrating. As the compound elutes to the collection chamber it passes from the high-pressure side to the low-pressure side. It is possible that there is minimal or no pressure change after elution from the column. When there is a pressure transition, there may be phase change, where the compressed fluid may change to gas due to process conditions or change maybe forced to achieve multiple phases for better collection. Detection of the component can be accomplished through the use of one or more of the following detectors, namely Mass spectroscopy detector, UV/VIS detector, Evaporative Light Scattering Detector, Flame Ionization detector, Fourier Transform Infrared Spectroscopy Detector and Infrared Detector. The nature of the detection does not limit the practice of the present invention. Any type new or existing can be used with the present invention.

The collection chamber of the cryofocusing system can be empty, packed or filled with material for enhancing adsorption/absorption or further separation. The eluted compound is concentrated or adsorbed in a collection chamber that is cooled as a result of process conditions and/or additional cooling. As the compound is being retained in the collection chamber, the process stream comprised of compressed fluid, gas or co-solvents is passed from the collection chamber to a waste or vent port for removal. The concentrated or adsorbed compound is then desorbed for further processing using a concentrating method. During the collection, the collection chamber is rinsed with desired solvent of defined volume after rapid heating of the collection chamber to ambient or higher temperature. The concentrating method involves static mode rinsing or continuous flow rinse to maximize the solvent or the solvent mixture's capability to remove or desorb the compound. The desorbed compound, dissolved or otherwise carried by the concentrating solvent is directed downstream to collection vials or another collection and sorting mechanism. During the desorbing process, the solvent may also be displaced from the collection chamber with the aid of a gas. The cleaning of the collection chamber is achieved by rinsing forward or backward. Additional purging with a gas may be used for drying the collection chamber. After the cleaning step, the collection chamber is ready to accept next eluted compound or compounds from the process in the proper sequence.

The chromatographic column exit stream may contain a compressed fluid which may be selected from a group consisting of carbon dioxide, water, ammonia, nitrogen, nitrous oxide, methane, ethane, ethylene, propane, butane, n-pentane, benzene, methanol, ethanol, isopropanol, isobutanol, monofluoromethane, trifluoromethane, dimethyl sulfoxide, acetonitrile, hydrofluorocarbons, chlorotrifluoromethane, monofluoromethane, hexafluoroethane, 1,1-difluoroethylene, 1,2-difluoroethylene,toluene, pyridine, cyclohexane, m-cresol, decalin, cyclohexanol, 0-xylene, tetralin, aniline, acetylene, chlorotrifluorosilane, xenon, sulfur hexafluoride, propane and combinations thereof. The compressed fluid may be at or near supercritical conditions.

The stream may also contain more than one solvents or cosolvents. The present invention can be practiced with any other solvent or compressed fluid in the exit stream. Above list is only shown for representative reasons. In a preferred embodiment, carbon dioxide is used in the exit stream. Cooling of the collection chamber to sub-ambient conditions can be accomplished either by the aid of pressure reduction or by the use of independent cooling like electric cooling, liquid nitrogen cooling, peltier cooling or other fluidic cooling. Heating of the collection chambers during the washing can be accomplished by one or more of the following methods, namely electrical or other fluidic heating. Such cooling and heating are designed to occur in a reasonably rapid manner. Temperature of the collection chamber at any point can be controlled with the use of the heating and cooling mechanisms provided in the present invention.

Collection chamber can be either a simple container or it can be packed with material of a different nature. Highly absorbing or adsorbing material can be used to retain the compounds efficiently. Optionally, such materials can be in particulate form providing enhanced surface area. Such packing material can be chemically active or simply physically active. Liquefied or frozen gas can also be used to trap the compounds in the collection chamber. In another embodiment, a removable cartridge type inner housing can be designed that can be accommodated inside the collection chamber. Such cartridges can be packed with the above mentioned materials. This allows for physical removal of the cartridge to collect compounds and separate washing of those compounds in a flexible way.

All mechanisms described including a detector, pressure regulator/orifice, valves, collection chambers, cooling/heating mechanisms, vial arrangements or sorting mechanisms are in communication for proper coordination of the steps to be executed. Such coordination can be automated using mechanical arrangements, electrical or pneumatic pulses, logic controllers, microprocessors and software programs.

FIG. 1 illustrates the present invention in its most simplistic embodiment with three collection chambers. The cryofocusing system can comprise of one or more collection chambers to accommodate collection capability as required. The figure does not include equipment needed for pre or post processing such as the chromatography system or sorting or downstream collection system. They are independent of the present invention.

The present invention is described in the following paragraph with respect to the drawings. For representative reasons, three collection chambers are described. It is not a limitation on the present invention. Multiple collection chambers can be used with the present invention. Chromatographic exit stream containing the desired compound(s) from the packed column and detector enter the automated back pressure regulator/orifice 1. The optional pressure reduction may be achieved at this orifice. Automated valve 2 receives the input stream and based on sequence and programming, it directs the stream to one of the three collection chambers 3, 4 or 5 that is available to receive the stream for concentrating the compound or compounds. Check valves 6, 7 or 8 and appropriate plumbing ensure the flow path from the automated valve 2 to the selected collection chamber. The check valves allow flow only in the downstream direction and avoid cross contamination. Rapid cooling to sub-ambient conditions either through the aid of pressure reduction of the stream or through independent cooling allows the compound to deposit inside the collection vessel. In another embodiment, additional packing materials of different forms can be used to enhance the retention of the compounds in the collection vessel. Collection chambers have the facility to vent or discharge process fluid through ports 18, 19 and 20 leaving the compounds collected in the chambers. Cooling and heating mechanisms 9, 10, and 11 with temperature sensor(s) rapidly cool or heat collection chambers 3, 4 or 5 as required during the sequence. Collection chambers are washed with a solvent while the chambers are simultaneously heated to desorb and remove the compounds from the collection chambers. One or more pumps 12 deliver the desired solvent from a solvent reservoir to automated valve 17. The automated valve 17 directs the flow to another automated valve 13 that selects the collection chamber in use for washing. The washed liquid containing solvents and the collected compound or a mixture of compounds at a high concentration is collected through the exit ports 18, 19 and 20.

In an additional embodiment, such washing can be accomplished by letting the solvent stream enter either at the top of the chamber and leave at the bottom ports or enter at the bottom ports and leave at the top or a combination thereof. This ensures efficient removal of the collected compounds from the collection chambers. Collected washings can be optionally collected in vials for further processing. It is possible to define the amount, nature and composition of the washing solvent. This provides the flexibility to obtain a desired concentration of the resultant solution containing the desired compounds. After the washings are collected, the collection chambers can be cleaned with a suitable solvent or a combination of solvents and further dried with inert gases like nitrogen, argon or simply air. Such cleaning can be more efficient when the solvents are flown in both forward and backward directions.

In a preferred embodiment, washing is accomplished by pumping the solvent using valves, a pump and a liquid reservoir(s) that are in communication with the collection chamber and the pressure regulator/orifice. Depending on the collection chamber to be washed, the automated valve 13 directs the solvent flow appropriately. Check valves 14, 15 and 16 allow flow from the automated valve 13 to the respective collection chambers. The automated valve 17 allows the use of an inert gas like air or nitrogen to displace concentrating solvent and dry the collection chambers. In its selected position, valve 17 allows solvent or gas to flow to valve 13.

In another embodiment, the automated valve 2 is switched to another collection chamber while the present collection chamber is in washing mode. This allows the present invention to be practiced in a continuous mode.

Only one solvent pumping system is shown for describing the present invention. In another embodiment, using solvent selection and mixing valves, multiple solvents can be selected from multiple reservoirs and mixed with defined compositions. This allows the use of best solvent composition to achieve the desired concentration of the resultant solution of the compounds.

The following examples illustrate the practice of the invention clearly.

EXAMPLE 1

A commercial analytical supercritical fluid chromatography system was used along with the present invention. The desired compound in the chromatographic column exit stream was trans-stylbene oxide(TSO). Several injections were made and the material was collected using the present invention. The mobile phase used was carbon dioxide and methanol (8 vol. %). The experimental parameters used during collection and flushing steps were as follows:

TABLE 1

| STEP I. Collection step | |
|---|---|
| Temperature in the Collection Chamber | −25° C. |
| STEP II. Washing step | |
| Temperature in the Collection Chamber | 70° C. |
| Washing time | 8 Min |
| Solvent used | Methanol |

The results obtained are shown in Table I. In this case the collection efficiency was 98.4%. On the other hand the concentration of the solution increased approximately 9 times that of the initial concentration.

TABLE 2

| Total TSO injected (mg) | 39.85 |
|---|---|
| TSO non collected in step I (mg) | 0.60 |
| TSO collected in step II (mg) | 39.20 |
| TSO collected in step II (wt. %) | 98.40 |
| Total losses (wt. %) | 0.13 |

EXAMPLE 2

In this case an HPLC was used along with the present invention. The desired compound in the chromatographic column exit stream was phosphatidylcholine (PC-H) and the mobile phase used was ethanol:water (90:10 vol %). The experimental parameters using during collection and washing steps are as follows:

TABLE 3

| STEP I. Collection step | |
|---|---|
| Temperature in the trap | −5° C. |
| STEP II. washing step | |
| Temperature in the trap | 70° C. |
| Wash time | 10 Min |
| Solvent used | Methanol |

The results obtained are shown in Table 4. In this case the collection efficiency was 98.7%. On the other hand the concentration of the solution increased approximately 10 times that of the initial concentration. In both examples initial concentration is the concentration of the stream if it is collected with conventional methods.

TABLE 4

| Total PC injected (mg) | 48.00 |
|---|---|
| PC non collected in step I (mg) | 0.20 |
| PC collected in step II (mg) | 47.4 |
| PC collected in step II (wt. %) | 98.7 |
| Total losses (wt. %) | 0.83 |

We claim:

1. A method for collecting a desired compound from a chromatographic column exit stream comprising:

(a) directing the stream to a collection chamber
   (b) cooling the collection chamber to a sub-ambient condition
   (c) collecting the compound for a duration to concentrate in the collection chamber
   (d) heating the collection chamber
   (e) washing the collection chamber with a desired solvent
   (f) collecting the washing.

2. The method as in claim 1 wherein the stream is directed to more than one collection chambers depending on detection of the stream component.

3. The method as in claim 2 wherein the detection of the component is accomplished through the use of one or more of the detectors selected from the group consisting of Mass spectroscopy detector, UV/VIS detector, Evaporative Light Scattering Detector, Flame Ionization detector, Fourier Transform Infrared Spectroscopy Detector, Infrared Detector and combinations thereof.

4. The method as in claim 1 wherein the washing can be accomplished in both forward and backward directions for efficient removal from the collection chamber.

5. The method as in claim 1 wherein the stream is directed to more than one collection chambers depending on time.

6. The method as in claim 1 wherein the chromatographic exit stream contains a compressed fluid.

7. The method as in claim 6 wherein the chromatographic exit stream contains one or more solvents.

8. The method as in claim 6 wherein the compressed fluid is selected from the group consisting of carbon dioxide, water, ammonia, nitrogen, nitrous oxide, methane, ethane, ethylene, propane, butane, n-pentane, benzene, methanol, ethanol, isopropanol, isobutanol, monofluoromethane, trifluoromethane, dimethyl sulfoxide, acetonitrile, hydrofluorocarbons, chlorotrifluoromethane, monofluoromethane, hexafluoroethane, 1,1-difluoroethylene, 1,2-difluoroethylene,toluene, pyridine, cyclohexane, m-cresol, decalin, cyclohexanol, 0-xylene, tetralin, aniline, acetylene, chlorotrifluorosilane, xenon, sulfur hexafluoride, propane and combinations thereof.

9. The method as in claim 8 wherein the compressed fluid is carbon dioxide.

10. The method as in claim 6 wherein cooling of the collection chamber is accomplished through the pressure reduction of the compressed fluid.

11. The method as in claim 6 wherein the compressed fluid is at near or supercritical condition.

12. The method as in claim 1 wherein cooling of the collection chamber is accomplished through one or more of the following techniques: electric cooling, liquid nitrogen cooling, peltier cooling or other fluidic cooling.

13. The method as in claim 1 wherein the heating of the collection chamber is accomplished through electrical or fluidic heating.

14. The method as in claim 1 wherein the cooling is accomplished rapidly.

15. The method as in claim 1 wherein the heating is accomplished rapidly.

16. The method as in claim 1 wherein the collection chamber contains absorbing material.

17. The method as in claim 1 wherein the collection chamber contains adsorbing material.

18. The method as in claim 16 or 17 wherein the material inside the collection chamber is in particulate form.

19. The method as in claim 18 wherein the particles contain active or passive surface area for efficient retention.

20. The method as in claim 16 or 17 wherein the material inside the collection chamber is a liquefied or frozen gas.

21. The method as in claim 1 wherein the collection chamber contains a removable cartridge.

22. The method as in claim 21 wherein the cartridge is packed with one or more materials described in claim 16.

23. The method as in claim 1 wherein heating of the collection chamber facilitates the removal of the compound from the collection chamber.

24. The method as in claim 1 wherein the temperature of the collection chamber is controlled.

25. The method as in claim 24 wherein the temperature control is achieved through a combination of the heating and cooling means.

26. The method as in claim 1 wherein the amount of washing solvent to be used is defined.

27. The method as in claim 1 wherein the washings are collected in vials for further processing.

28. The method as in claims 17, 21 or 19–27 wherein the activities are automated through the use of mechanical arrangements, electrical or pneumatic pulses, logic controllers, microprocessors and software programs.

29. The method as in claims 1 through 27 wherein the collection chamber can be cleaned with a solvent and dried for subsequent use.

30. The method as in claim 29 wherein the cleaning can be accomplished through forward or backward flowing of the solvent.

31. The method as in claim 1 wherein the collection in the collection chambers is enhanced by pressure reduction.

* * * * *